(12) United States Patent
Viellerobe et al.

(10) Patent No.: US 7,869,679 B2
(45) Date of Patent: Jan. 11, 2011

(54) MODULAR IMAGING SYSTEM, MODULES FOR THIS SYSTEM AND METHOD IMPLEMENTED USING THIS SYSTEM

(75) Inventors: Bertrand Viellerobe, Nogent sur Marne (FR); Francois Lacombe, Chaville (FR); Nicolas Boularot, Le Perreux sur Marne (FR); Francois Doussoux, Paris (FR); Nicolas Lavillonniere, Saint Maur les Fosses (FR)

(73) Assignee: Mauna Kea Technologies, Paris (FR)

( * ) Notice: Subject to any disclaimer, the term of this patent is extended or adjusted under 35 U.S.C. 154(b) by 106 days.

(21) Appl. No.: 12/249,665

(22) Filed: Oct. 10, 2008

(65) Prior Publication Data
US 2009/0097806 A1    Apr. 16, 2009

(30) Foreign Application Priority Data
Oct. 11, 2007    (FR) .................................... 07 58236

(51) Int. Cl.
*G02B 6/06* (2006.01)
(52) U.S. Cl. ........................ 385/116; 385/117; 600/182

(58) Field of Classification Search ....................... None
See application file for complete search history.

(56) References Cited

U.S. PATENT DOCUMENTS

| 5,659,642 A * | 8/1997 | King et al. ..................... 385/16 |
| 6,370,422 B1 * | 4/2002 | Richards-Kortum et al. 600/478 |
| 7,385,692 B1 * | 6/2008 | Nguyen ....................... 356/301 |
| 2005/0020926 A1 * | 1/2005 | Wiklof et al. ................ 600/476 |

* cited by examiner

*Primary Examiner*—Hemang Sanghavi
(74) *Attorney, Agent, or Firm*—Osha • Liang LLP

(57) ABSTRACT

An imaging device includes an illumination module comprising at least one emitter for emitting at least one excitation beam; a scanning and injection module comprising an image guide, a proximal end and a distal end of which are linked by a plurality of optical fibers; a scanning and injection optical system configured to alternately inject the at least one excitation beam into an optical fiber of the image guide from the proximal end of the image guide; a detection module comprising a detector for detecting a luminous flux collected at the distal end of the image guide, wherein at least one of the illumination module and the detection module is optically conjugated with the scanning and injection module using a conjugating optical fiber.

32 Claims, 6 Drawing Sheets

MODULAR IMAGING SYSTEM, MODULES FOR THIS SYSTEM AND METHOD IMPLEMENTED USING THIS SYSTEM

REFERENCE TO RELATED APPLICATIONS

This claims benefits, under 35 U.S.C. §119, of French Application No. 0758236 filed on Oct. 11, 2007.

TECHNICAL FIELD

The present invention relates to a device for imaging by proximal scanning of a bundle of optical fibers. It also relates to a module for this device and a method implemented by this device.

The field of the invention particularly relates to endoscopy and fibered confocal microscopy.

PRIOR ART

There is a known document WO 06 000 704 A1 that describes a system for fluorescence microscopic imaging by proximal scanning of a bundle of optical fibers.

Such a system comprises lasers that emit excitation beams and an array of dichroic filters, beam splitters, and lenses that guide the excitation beams to scanning means, which alternately inject the excitation beams into a fiber of an image guide from the proximal end of the guide. The guide is made to guide the excitation beams to its distal end placed in contact with or in proximity to a sample. In response to the excitation beams, the sample emits a luminous response flux, collected by the distal end of the guide. The collected flux is guided along the guide, then through the scanning and injection optical system and the array of filters, beam splitters and lenses, to a detector. A filtering hole in front of the detector makes it possible to reject the light that may have been coupled into the fibers of the guide adjacent to those transporting the excitation beams. Thus, only the part of the collected flux that has been guided along the fiber transporting the excitation beams is imaged in the detector.

The optical alignment of the filtering hole relative to the position of the fibers of the guide on the proximal end of the guide is critical because it guarantees the confocality of the system. Such an alignment is complex to achieve, since the typical diameter of the fibers of the guide is a few micrometers. This alignment specifically depends on all of the optical components located between the filtering hole and the image guide.

The technical characteristics of certain optical components of the system strongly depend on the wavelengths of the excitation beams used, particularly the characteristics of the dichroic filters. A first problem with this system is that the laser sources and the dichroic filters are difficult to access in order to change the wavelength of an excitation beam, and it is generally preferable to replace the system entirely.

A second problem with such a system is that it is nearly impossible to replace or reposition an optical component of the system, or to add a new optical component to the system, without having to realign the entire system. In particular, if the system is not realigned, its runs the risk of losing its confocality.

The object of the present invention is to propose a device that makes it possible to solve all or some of the above-mentioned problems, and a method implemented by such a device.

BRIEF DESCRIPTION OF THE INVENTION

This object is achieved with an imaging device comprising:
an illumination module comprising at least one emitter for emitting at least one excitation beam,
a scanning and injection module comprising an image guide, a proximal end and a distal end are linked by a plurality of optical fibers, and a scanning and injection optical system configured to alternately inject the at least one excitation beam into an optical fiber of the image guide from the proximal end of the image guide,
a detection module comprising a detector for detecting a luminous flux collected at the distal end of the image guide,
at least one of the illumination module and the detection module being optically conjugated with the scanning and injection module by a conjugating optical fiber.

In this description, two objects are said to be optically linked or conjugated when at least one optical flux, signal or beam can be guided from one object to the other. One of these objects can consist, for example, of one of the modules or one of the fibers of the device according to embodiments of the invention.

In this description, when two objects are optically conjugated by a main optical element (this main element typically comprising an optical fiber), there may be other, intermediate optical elements conjugating the objects with the main optical element. The conjugating fiber can comprise an illuminating fiber, a detecting fiber, or a splitting fiber, all of which will be described below.

The conjugating optical fiber, for a given position of the scanning and injection optical system, can be optically conjugated with a single optical fiber of the image guide.

A device according to embodiments of the invention can comprise means for disconnecting and reconnecting the conjugation via the conjugating optical fiber, such as a connector.

The illumination module can be optically conjugated with the scanning and injection module by an illuminating optical fiber. The illuminating optical fiber can be made to perform a mode filtering of the at least one excitation beam, and is preferably a single-mode optical fiber. The at least one emitter may comprise a plurality of emitters each comprises a source for emitting an excitation beam, and the illumination module may comprise a device (i.e., a multiplexer) for multiplexing the excitation beams in the illuminating optical fiber. Each source can be optically conjugated with the multiplexing means by a source optical fiber, and the multiplexing means can comprise, for example, a fiber multiplexer that fuses the cores of the source fibers, or non-fiber multiplexing means, for example comprising acousto-optical multiplexing systems, or a phasar-type multiplexer. Preferably, the illuminating optical fiber is made to be alternately optically conjugated with a single fiber of the image guide, into which the at least one excitation beam is injected by the scanning and injection optical system.

Likewise, the detection module can be optically conjugated with the scanning and injection module by a detecting optical fiber. The scanning and injection optical system can be made to guide the collected luminous flux to the detection module. The detecting optical fiber can be made to perform a spatial filtering of the collected luminous flux. The detecting optical fiber, for a given position of the scanning and injection optical system, can be optically conjugated with the fiber of the image guide, into which the scanning and injection optical system is configured to inject the at least one excitation beam, and can be made to reject the light coming from the other fibers of the image guide. The detecting optical fiber is preferably a multi-mode optical fiber. Preferably, the detecting optical fiber is made to be alternately optically conjugated with a single optical fiber of the image guide, into which the at least one excitation beam is alternately injected by the scanning and injection optical system.

Generally, the detection module can comprise a device (i.e., demultiplexer) for wavelength demultiplexing the collected luminous flux. The detection means can comprise several detectors, each detector being made to detect a given wavelength band of the demultiplexed flux.

The scanning and injection optical system can be made to guide the luminous flux collected at the distal end of the image guide to the detection module, and the device according to embodiments of the convention can comprise a beam splitter configured to direct the at least one excitation beam to the scanning and injection optical system, and to direct the collected luminous flux coming from the scanning and injection optical system to the detection module. The beam splitter can comprise, for example, a dichroic filter, preferably a multiband filter. The beam splitter may also comprise a beam-splitting cube, such as, preferably, a polarizing cube. The illumination module and the detection module in that case preferably are provided, in particular, for reflectance imaging of a sample. In a variant, the beam splitter may be part of the scanning and injection module. In another variant, the beam splitter may be part of a splitting module. The detection module and the illumination module may be optically conjugated with the scanning and injection module by the splitting module and a splitting optical fiber. The splitting optical fiber may conjugate the splitting module with the scanning and injection module, while an illuminating or detecting fiber may conjugate the illumination or detection module, respectively, with the splitting module. In one embodiment, the splitting optical fiber can comprise a sole single-mode or multi-mode fiber, depending on whether the goal is to optimize the quality of the excitation beam or the collected flux, respectively. In another embodiment, the splitting optical fiber can comprise a two-core fiber comprising two substantially concentric fiber cores, the first of the two cores having a smaller diameter than the second of the two cores, each of the cores being either single-mode or multi-mode. Preferably, the first core is single-mode and is made to transport the at least one excitation beam, and the second core is multi-mode and is made to transport the collected luminous flux.

According to yet another aspect of the invention, a scanning and injection module is proposed for a device according to the invention, said module comprising:

an image guide comprising a proximal end and a distal end linked by a plurality of optical fibers, a conjugation means provided for optically conjugating the scanning and injection module with an illumination module comprising at least one emitter for emitting at least one excitation beam, and with a detection module comprising a detector for detecting a luminous flux collected at the distal end of the image guide, a scanning and injection optical system made to alternately inject the at least one excitation beam into a fiber of the image guide from the proximal end of the guide, the conjugation means being made so that at least one of the illumination module and the detection module is optically conjugated with the scanning and injection module by a conjugating optical fiber.

The conjugation device (e.g., connector) can be made so that the conjugating fiber, for a given position of the scanning and injection optical system, is optically conjugated with a single fiber of the image guide.

In a variant, the conjugating fiber can be integral with the module. Thus, the conjugation device may comprise the conjugating optical fiber.

In another variant, the conjugation device can comprise means, such as a connector, for disconnecting the conjugating fiber from the scanning and injection module and reconnecting the conjugating fiber to the scanning and injection module.

The conjugation device can comprise means for optically conjugating the scanning and injection module with the illumination module via an illuminating optical fiber, and these conjugation device can be made so that the illuminating fiber, for a given position of the scanning and injection optical system, is optically conjugated with the fiber of the guide into which the scanning and injection optical system is configures to inject the at least one excitation beam, and is not optically conjugated with the other fibers of the image guide.

In addition, the conjugation device can comprise means for optically conjugating the scanning and injection module with the detection module via a detecting optical fiber, the scanning and injection optical system can be made to guide the collected luminous flux to the detection module, and the conjugation device can be made so that the detecting fiber, for a given position of the scanning and injection optical system, is optically conjugated with the fiber of the guide into which the scanning and injection optical system is configured to inject the at least one excitation beam, and is not optically conjugated with the other fibers of the image guide.

According to yet another aspect of the invention, an imaging method implemented in the device according to the invention is proposed, and comprises:

emitting, by using an illumination module, at least one excitation beam, alternately injecting, by using a scanning and injection module, the at least one excitation beam into a fiber of an image guide comprising a proximal end and a distal end linked by a plurality of optical fibers from the proximal end of the guide, detecting, by using a detection module, a luminous flux collected at the distal end of the guide, and optically conjugating, by using a conjugating optical fiber, the illumination module and/or the detection module with the scanning and injection module.

In this description, a step for the optical linking or conjugation of two objects comprises guiding at least one optical flux, signal or beam from one object to the other. One of these objects can consist, for example, of one of the modules or one of the fibers of the device according to the invention.

The optical conjugation with the scanning and injection module can comprise an optical conjugation of the conjugating optical fiber with a single fiber of the guide.

The optical conjugation with the scanning and injection module can comprise guiding the at least one excitation beam from the illumination module to the scanning and injection module along an illuminating optical fiber. A method according to one embodiment of the invention can comprise modal filtering the at least one excitation beam by the illuminating fiber. A method according to one embodiment of the invention can also comprise spatially superpositioning or multiplexing several excitation beams in the illuminating fiber.

The optical conjugation with the scanning and injection module can comprise guiding the collected flux from the scanning and injection module to the detection module along a detecting optical fiber. A method according to one embodiment of the invention can comprise spatially filtering, by using the detecting fiber, the collected flux, so that the detecting optical fiber is alternately optically conjugated with the fiber of the image guide into which the at least one excitation beam is alternately injected.

A method according to embodiments of the invention can also comprise wavelength demultiplexing, by using the detection module, the collected luminous flux.

A method according to embodiments of the invention can also comprise guiding, by using the scanning and injection optical system, the collected luminous flux to the detection module; guiding, by using a beam splitter, the at least one excitation beam to the scanning and injection optical system; and guiding, by using the beam splitter, the collected luminous flux coming from the scanning and injection optical system to the detection module.

Coupling between the fibers of an image guide is intended to mean a transmission of light along the guide between a first fiber of the guide and a second fiber of the guide adjacent to the first fiber. In general, any coupling effects between the fibers of the image guide, particularly when it the conjugating optical fiber is said to be optically conjugated with a single fiber of the guide, has been omitted from the description of the invention: the coupling between this single fiber and the fibers of the guide adjacent to this single fiber are not taken into consideration. Preferably, the image guide of the device, method or module according to the invention is made so that there is no appreciable coupling between the fibers of the image guide.

DETAILED DESCRIPTION OF THE FIGURES AND EMBODIMENTS

Other characteristics and advantages of the invention will emerge through the reading of the detailed description of nonlimiting embodiments and implementations and the attached drawings, in which.

Figure 1:
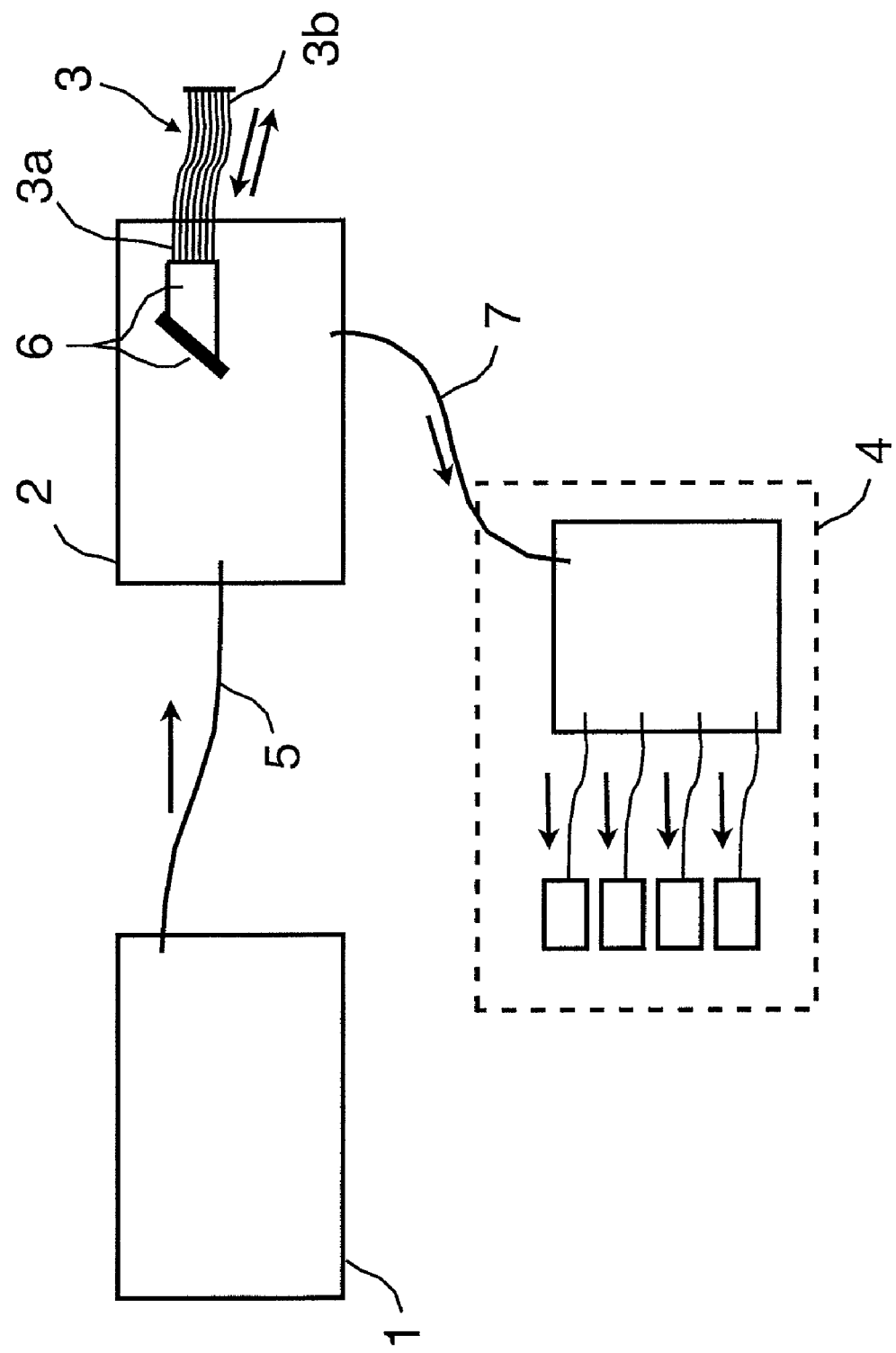
FIG. 1 is a schematic view of a device according to the invention.

We will first describe, in reference to FIG. 1, a device according to one embodiment of the invention whose features are common to the various embodiments that will be described below and that implement methods according to embodiments of the invention.

The device comprises an illumination module 1, a scanning and injection module 2, and a detection module 4. Typically, an image guide included in the scanning and injection module may comprise several thousand fibers, each with a diameter of a few micrometers.

The illumination module 1 comprises at least one emitter for emitting at least one excitation beam, and is optically conjugated with the scanning and injection module 2 by means of an illuminating optical fiber 5. When the illumination module 1 emits the at least one excitation beam, this excitation beam is guided along the illuminating fiber 5 to the scanning and injection module 2.

The scanning and injection module comprises an image guide 3 that has a proximal end 3a and a distal end 3b linked by a plurality of optical fibers, which may be multi-mode optical fibers. The scanning and injection module 2 also comprises an optical system 6 for alternately scanning and injecting the at least one excitation beam into a fiber of the image guide 3 from the proximal end 3a of the guide. In this description, a "position of the scanning and injection optical system" is intended to mean a state of the scanning and injection optical system 6 wherein these means are made to inject the at least one excitation beam into a given fiber of the image guide 3, the scanning and injection optical system successively assuming several positions so as to periodically scan all the fibers of the guide. This at least one excitation beam is then guided through this fiber of the guide to the distal end 3b of the image guide 3. The distal end 3b is provided in order to be placed into, or in contact with, a sample, and to collect a luminous flux emitted by the sample. The collected flux can, for example, comprise reflectance and/or fluorescence signals, respectively emitted by the sample by reflectance and/or by fluorescence in response to the at least one excitation beam that this sample has received. Reflectance means an emission of light by diffusion or by retrodiffusion. The image guide 3 thus typically forms an endoscopic probe, the distal end 3b of which may or may not be equipped with an optical head.

The scanning and injection module 2 is optically conjugated with the detection module 4 by means of a detecting optical fiber 7. The luminous flux collected by the distal end 3b is guided to the proximal end 3a, and then guided to the input of the detecting optical fiber 7. The collected luminous flux is then guided along the detecting fiber 7 to the detection module 4.

The detection module 4 comprises a detector for detecting the luminous flux collected at the distal end 3b.

A first function of the illuminating 5 and detecting 7 fibers conjugating the modules 1, 2, 4 is to function as a bridge between these modules, and thus to separate the main internal functions of the device, i.e. the illumination, scanning and injection, and detection functions, by associating each of these internal functions with one of the modules 1, 2, 4. Thus, these separate functions are easier to repair. The use of the fibers 5, 7 makes it easy to access the components of the device, for example in order to replace an optical component inside one of the modules 1, 2, 4 or to align the optical components inside one of the modules with each other, without thereby running the risk of throwing the entire device out of optical alignment.

In addition, the ends of the fibers 5, 7 are removably attached to connectors so that the conjugation between the illumination module 1 and the scanning and injection module 2 by means of the illuminating fiber 5, and the conjugation between the detection module 4 and the scanning and injection module 2 by means of the detecting fiber 7 can be disconnected and reconnected. The various modules 1, 2, 4 of the device according to the invention can therefore be separated from the rest of the device. This makes the separate functions easier to replace. Any of the modules 1, 2 4 can therefore be replaced quickly without having to replace the entire device, which is a cost advantage, and without having to optically realign the modules with each other.

The fiber conjugations 5, 7 between modules 1, 2, 4 also makes it possible to add other modules to the device according to the invention, or more generally to upgrade the device without having to replace it in its entirety. It is possible, for example, to replace the illuminating fiber 5 with an array of optical components that are optically conjugated with the illumination module 1 by one optical fiber and optically conjugated with the scanning and injection module 2 by another optical fiber, or to replace the detecting fiber 7 with an array of optical components that are optically conjugated with the detection module 4 by one optical fiber and optically conjugated with the scanning and injection module 2 by another optical fiber.

Thus, the architecture in the form of modules associated with separate functions and optically conjugated by optical fibers makes it possible to reduce the costs and lead times of the device according to the invention and to improve the maintenance, repair and upgrading of the device according to the invention.

In addition, when the illuminating optical fiber 5 is a single-mode, preferably Gaussian, optical fiber, the mode of the single-mode fiber 5 being selected so as to efficiently excite one or more modes of the guide 3. Thus, the fiber 5 gives the at least one excitation beam a high single-mode Gaussian quality. Moreover, the rate of injection of the at least one excitation beam into the image guide 3 is optimal because the PSF ("Point Spread Function") on injection into the guide is provided so as to correctly correspond to the fundamental mode of the optical fibers of the guide.

Finally, the illuminating optical fiber 5, for a given position of the scanning and injection optical system, is made to be optically conjugated with a single fiber of the guide 3, more particularly with the fiber of the guide into which the scanning and injection optical system is configured to inject the at least one excitation beam. For a given position of the scanning and injection optical system 6, the at least one excitation beam transported by the illuminating fiber 5 is only injected into one fiber of the guide. In particular, the diameter of the illuminating fiber 5 and the position of the end of the illuminating fiber 5 oriented toward the scanning and injection module 2 depend on the diameter of the fibers of the guide 3, the position of the proximal end 3a of the guide, and the characteristics of the optical components disposed between the illuminating fiber 5 and the scanning and injection optical system 6.

The detecting optical fiber 7 is preferably a multi-mode optical fiber. In essence, the luminous flux collected by the distal end 3b, for example emitted by reflectance or by fluorescence, generally excites numerous modes of the fibers of the guide. Thus, the detecting fiber 7 transports the luminous flux collected by the guide 3 with nearly no signal loss. Thus, according to preferred embodiments, another function of the detecting fiber 7 is not to perform any mode filtering on the flux collected by the guide 3.

Moreover, the detecting optical fiber 7, for a given position of the scanning and injection optical system, is made to be optically conjugated with a single fiber of the image guide 3. In other words, for a given position of the scanning and injection optical system 6, the detecting fiber 7 transports to the detection module only the part of the luminous flux collected at the distal end 3b that has been guided along this single fiber of the guide 3. The detecting fiber 7 makes it possible to reject the parts of the collected flux that have been guided along the other fibers of the guide. As with the illuminating fiber 5, the diameter and the position of the end of the detecting fiber 7 oriented toward the scanning and injection module should be adjusted accordingly. Preferably, the detecting optical fiber, for a given position of the scanning and injection optical system, is optically conjugated with the fiber of the guide into which the scanning and injection optical system inject the at least one excitation beam. The detecting fiber 7 therefore makes it possible, for a given position of the scanning and injection optical system, to reject the parts of the collected flux that have been guided along fibers other than the one guiding the excitation beams. Thus, the detecting fiber 7 functions as a filtering hole. The detecting fiber 7 therefore has the function of spatially filtering the flux collected at the distal end 3b. The detecting fiber 7 makes it possible to select the fiber of the guide 3 that has been used for the illumination (i.e. for the transport of the at least one excitation beam), thus enabling the device according to the invention to retain its confocality. This confocality is initially due to an optical conjugation of a point of the sample with only the fiber of the guide that guides an excitation beam exciting this point on the sample.

The scanning and injection optical system 6 are made to alternately inject the at least one excitation beam into a fiber of the image guide 3, in such a way as to periodically scan all the fibers of the guide. By alternately injecting the excitation beams into a fiber of the guide 3, the detection means of the detection module 4 alternately detect the luminous flux collected by the distal end 3b and guided along this fiber of the guide, which comes from a source point of the sample. When the scanning and injection optical system has scanned all the fibers of the guide, the detection means have scanned a set of source points of the sample, i.e. an entire field of vision of the sample. The detection means (detectors) are linked to means for constructing, from this scanning of the field of vision, an image of the sample. The construction means can construct a reflectance or fluorescence image of the sample, depending on the nature of the signals of the collected luminous flux. The detection means are also linked to means for displaying the constructed image. The size of the field of vision depends on the number of fibers in the image guide, on the diameter of these fibers, and possibly on the characteristics of the optical head disposed on the distal end of the guide if this head exists. Typically, the guide comprises several thousand fibers having a diameter of a few micrometers. The field of vision therefore typically measures from one to a few hundred micrometers per side. The device according to the invention is therefore particularly adapted to fibered confocal fluorescence and/or reflectance microscopy.

Figure 2:
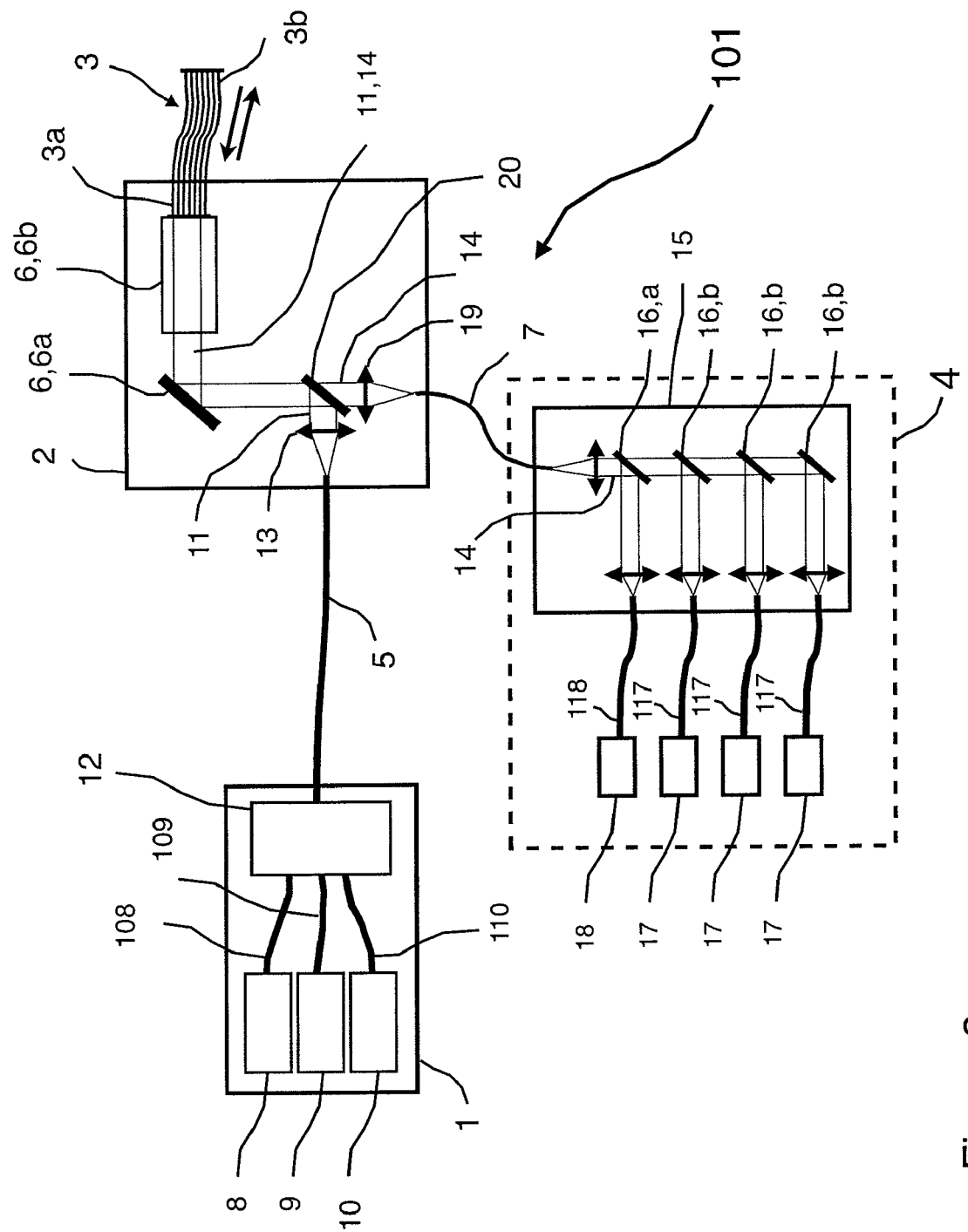
FIG. 2 is a more detailed view of a first embodiment of a device according to the invention.

We will now describe, in reference to FIG. 2, a first embodiment of a device 101 according to the invention, particularly applied to fluorescence detection, quantification or imaging. Since this embodiment has all of the characteristics of the device just described in reference to FIG. 1, references 1 through 7 will not be described again.

The illumination module 1 may comprise several excitation sources 8, 9, 10, each corresponds to an emitter. These excitation sources may be laser sources, each of which emits an excitation beam having a different wavelength or wavelength band than the other excitation beams. The device 101 also comprises a multiplexer for multiplexing the sources 8, 9, 10 inside the illuminating optical fiber 5. Thus, the illuminating optical fiber 5 makes it possible to spatially superpose all of the excitation beams 11 at the input of the scanning and injection module 2.

Each source 8, 9, 10 is optically conjugated with a multiplexer 12 by a respective source fiber 108, 109 or 110, which transports the excitation beam emitted by said source. The multiplexer 12 may be a fiber multiplexer made to fuse the cores of the source fibers 108 through 110 into a single fiber of which the illuminating fiber 5 is the extension. At the input of the scanning and injection module 2, the excitation beams 11 are collimated by an optical system 13.

For the same reasons as the illuminating fiber 5, the source fibers 108 through 110 are preferably single-mode fibers. Thus, the fibers 108 through 110 give each excitation beam a high single-mode Gaussian quality and provide an optimal rate of injection of each excitation beam into the image guide 3. Each source fiber therefore allows mode filtering of an excitation beam.

The illumination module 1 comprises a package in which are grouped the sources 8 through 19, the source fibers 108 through 110 and the multiplexer 12. The illuminating fiber 5 can be disconnected from and reconnected to the package of the illumination module 1 by means of a connector or a similar device. Likewise, the source fiber 108 through 110 can be disconnected from and reconnected to the respective source 8 through 10, making it possible to replace this source and thereby change the wavelength or wavelength band of the excitation beam emitted by this source.

The detection module 4 may comprise a demultiplexer for wavelength demultiplexing the luminous flux 14 collected at the distal end of the guide 3. The demultiplexing means 15 comprise several dichroic filters 16a, 16b. Each dichroic fiber 16a or 16b returns a different wavelength of the flux 14 to a detector 17 or 18. Thus, each detector 17 or 18 is made to detect a different wavelength band of the flux 14 and makes it possible to image the sample by means of fluorescence signals whose wavelength is contained in this band and collected by the distal end 3b.

The detection means may comprise at least one detector 17 or 18 per source 8 through 10 and hence per excitation beam wavelength band. Each detector 17 or 18 may be associated with an excitation beam. In essence, the wavelength band of each detector 17 or 18 preferably corresponds to the emission band of a fluorophore excited at the wavelength or wavelength band of the excitation beam associated with said detector. In the example illustrated in FIG. 2, the device 101 comprises three sources 8 through 10 and four detectors 17 and 18, since several wavelength bands of the flux 14 can be linked to the same excitation beam wavelength or wavelength band, said excitation beam being able to be adapted so as to excite several fluorophores.

Each dichroic filter 16a or 16b is associated with a demultiplexing fiber 117 or 118 made to guide the wavelength band returned by this dichroic filter to the detector 17 and 18. For the same reasons as the detecting fiber 7, the demultiplexing fibers are multi-mode optical fibers. For photometric reasons, for an optical enlargement equal to one in the array of optical components optically linking each demultiplexing fiber with the detecting fiber 7, the demultiplexing fibers each have a diameter greater than or equal to preferably greater than) the diameter of the detecting fiber 7, which allows for better optical alignment tolerance and also makes it possible to collect a maximum of flux, i.e. to limit photometric losses. If the optical enlargement is different from one, the demultiplexing fibers each have a diameter greater than or equal to preferably greater than) the diameter of the detecting fiber 7 adjusted by this optical enlargement.

The detecting fiber 7 may be connected to and disconnected from the detection module 4 by means of a connector or the like. Likewise, the detection module comprises means for disconnecting and reconnecting each multiplexing fiber 117, 118, thus making it possible to easily replace the detectors 17 and 18.

The scanning and injection module 2 comprises a package in which are grouped various optical systems 13, 19, the scanning and injection optical system 6, and means for splitting (beam splitter) the optical path of the excitation beams 11 from the optical path of the collected flux 14. The image guide 3 can be disconnected from the package of the scanning and injection module 2, thus making it possible to change the type of guide 3 connected to the package of the scanning and injection module 2. Among the various types of guides 3 are, for example, a guide whose fibers may be single-mode, a guide whose fibers are multi-mode, a guide with an optical head at its distal end, a guide without an optical head at its distal end, a guide with a given number of fibers, a guide with a given fiber diameter, or a guide with a given length between its proximal end and its distal end.

The splitting means may comprise a dichroic filter 20. The filter 20 may be a multiband filter, meaning that it can reflect several different wavelength bands and can transit several other wavelength bands. In the example illustrated in FIG. 2, the filter 20 reflects bands corresponding to the wavelengths of the excitation beams 11, and transmits bands corresponding to wavelengths of the collected flux 14 and to the bands reflected by the filters 16a, 16b and detected by the detectors 17 and 18. It is also possible to embody the device 101 with a filter 20 that reflects bands corresponding to wavelengths of the collected flux 14 and to the bands reflected by the filters 16a, 16b and detected by the detectors 17 and 18, and transmits bands corresponding to the wavelengths of the excitation beams, provided that the positions of the illuminating fiber 5 and the illumination module 1 are exchanged with the positions of the detecting fiber 7 and the detection module 4 and the optical systems 13 and 19 are inverted.

The luminous excitation beams 11 guided along the illuminating fiber 5 and collimated by the optical system 13 are directed by the splitting means to the scanning and injection optical system 6. The scanning and injection optical system 6 comprise two moving mirrors 6a which allow two-dimensional scanning in the plane of the input surface of the proximal end of the guide, and an optical system 6b. The moving mirrors 6a alternately inject the excitation beams into a fiber of the image guide. Before entering the guide 3, the excitation beams pass through the optical system 6b, which focuses them onto the proximal end of the guide 3.

In the opposite direction, the collected flux 14 is collimated by the optical system 6b, then directed by the moving mirrors 6a to the detection module 4. Between the moving mirrors 6a and the detection module 4, the collected flux 14 passes through the splitting means, is focused by the optical system 19 at the input of the detecting fiber 7, then guided along the detecting fiber 7 to the detection module 4.

The illuminating fiber 5 can be disconnected from and reconnected to the package of the scanning and injection module 2 by means of a connector. Likewise, the detecting fiber 7 can be disconnected from and reconnected to the package of the scanning and injection module 2 by means of a connector.

One drawback with the device 101 is that the spectral characteristics of the dichroic filter 20 located inside the package of the scanning and injection module 2, particularly for the wavelength bands it is designed to transmit or reflect, depend on the wavelengths of the excitation beams and of the collected flux. A change in the wavelength of one of the excitation beams may render it necessary to change the multiband filter 20, yet the latter is complicated to specify, produce and optically align inside the scanning and injection module.

Figure 3:
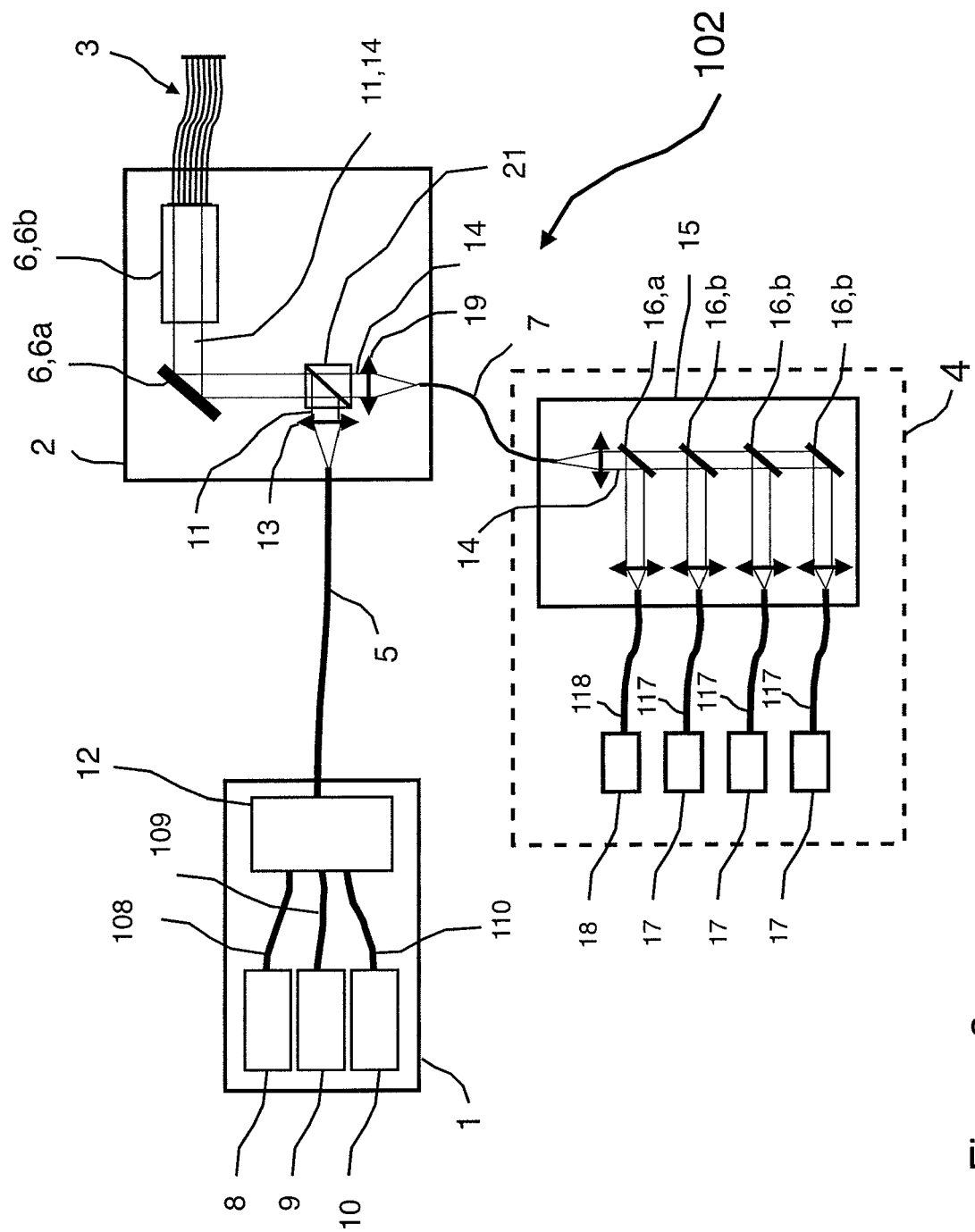
FIG. 3 is a view of a second, preferred embodiment of a device according to the invention.

We will now describe, in reference to FIG. 3, a second embodiment of a device 102 according to one embodiment of the invention that makes it possible to solve this problem. The device 102 is a preferred embodiment of the device according to embodiments of the invention that implements a preferred embodiment of the method according to the invention. The device 102 will be described only with respect to its differences from the device 101 described in reference to FIG. 2. In particular, the references 1 through 19, 108 through 110, 117 and 118 will not be described again. The device 102 makes it possible, in particular, to detect fluorescence or reflectance signals collected at the distal end of the guide, and makes it possible to quantify these signals and/or to construct images of the sample from these signals by fluorescence and reflectance.

In the device 102, the splitting means of the scanning and injection module 2 consist in a polarizing cube 21, which replaces the multiband dichroic filter. The polarizing cube 21 reflects beams having a first polarization and transmits the beams having a polarization orthogonal to the first polarization. All of the excitation beams 11 have the same polarization. The parasitic reflections of the excitation beams, for example at the level of the scanning and injection optical system 6 or the guide 3, have retained the same polarization as the excitation beams. On the other hand, the collected flux 14 coming from the distal part of the guide 3 may have lost the polarization state of the excitation beams, and therefore comprises signals having one or more random polarizations over time. The polarizing cube 21 may be made to direct the excitation beams 11 to the scanning and injection optical system 6, and to direct the collected luminous flux 14 to the detection module 4. In the example of FIG. 3, the cube 21 reflects the excitation beams 11 and the parasitic reflections, and transmits at least part of the collected flux 14. It is also possible to embody the device 102 with a cube 21 that reflects at least part of the collected flux 14 and transmits the excitation beams, provided that the positions of the illuminating fiber 5 and the illumination module 1 are exchanged with the positions of the detecting fiber 7 and the detection module 4. Thus, the cube 21 makes it possible to split the excitation beams and the parasitic reflections that have retained the polarization of the excitation beams, from the collected flux 14 coming from the distal part of the guide 3.

One of the filters 16a of the detection module 4 is embodied so as to direct to the detector 18 a wavelength band of the collected flux 14 comprising the wavelength or wavelength band of one of the laser sources 8. Thus, the detector 18 and the laser source 8 can be used for reflectance imaging of the sample located at the distal end of the guide. This is only possible because of the fact that the parasitic reflections are rejected by the cube 21. The other filters 16b of the detection module 4 and the associated detectors 17 make it possible, as in the first embodiment, to quantify fluorescence signals coming from the sample or to perform fluorescence imaging of the sample.

The use of the cube 21 has one disadvantage relative to the first embodiment of the device according to the invention. In essence, the use of the cube 21 results in losses in the intensity of the collected flux 14, particularly losses in the intensity of fluorescence signals. In essence, while the cube directs all of the intensity of the excitation beams 11 to the scanning and injection optical system 6 because of their polarization, the collected flux 14 is partially reflected and partially transmitted by the cube 21 because it does not have just one polarization. The collected flux 14 is therefore only partially directed to the detection module 4. Typically, 50% of the intensity of the collected flux 14 directed to the detection module 4 is lost. Thus, the sensitivity of the device 102 is reduced.

Moreover, in order not to lose intensity in the excitation beams 11 directed to the scanning and injection optical system, all of the fibers guiding the excitation beams 11 to the scanning and injection optical system 6 (i.e., the source fibers 108 through 110 and the illuminating fiber 5) are polarization maintaining fibers, resulting in an additional production cost and a specific adjustment.

Figure 4:
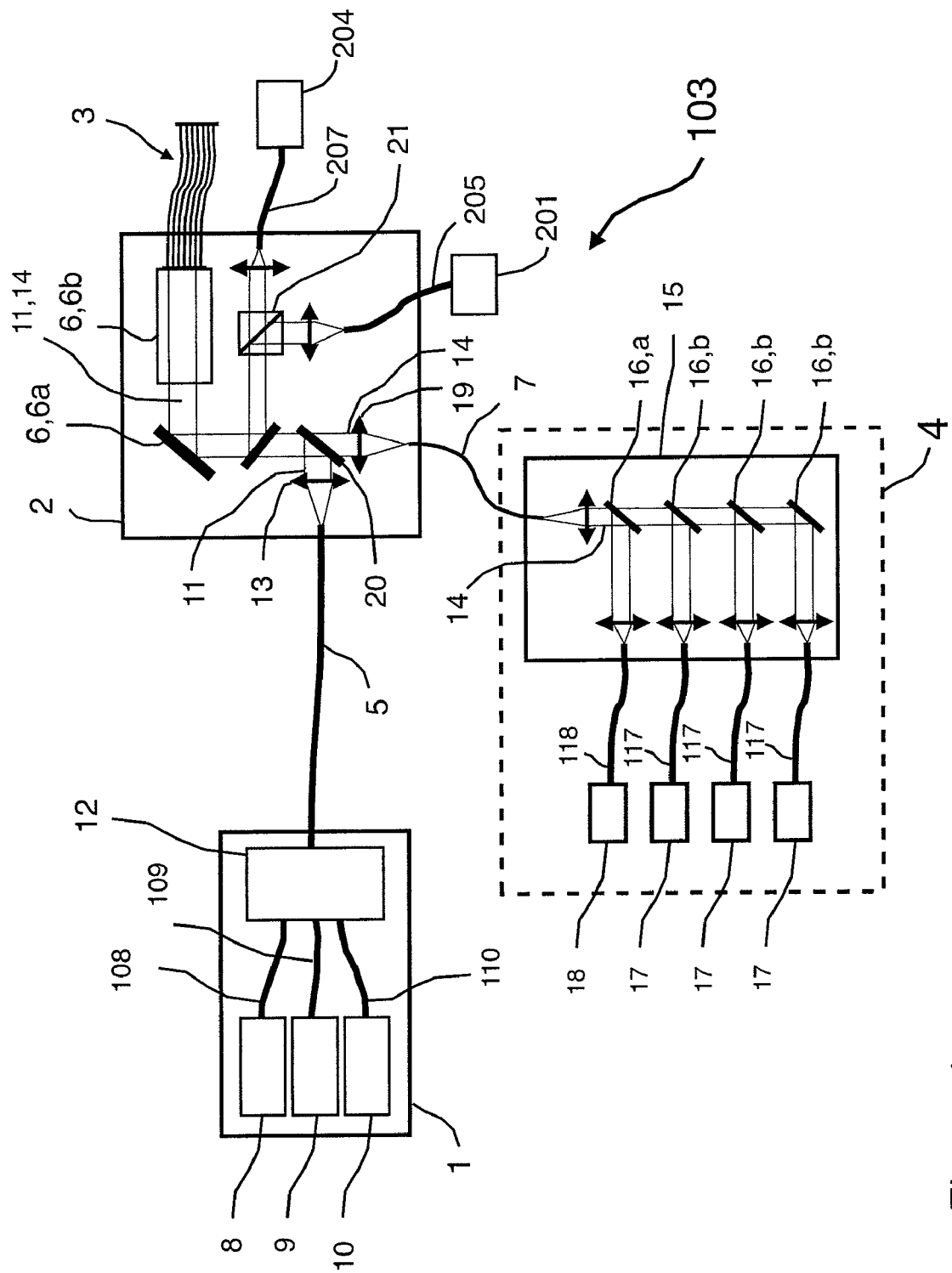
FIG. 4 is a view of a third embodiment of a device according to the invention.

We will now describe, in reference to FIG. 4, a third embodiment of a device 103 according to another embodiment of the invention. The device 103 will only be described with respect to its differences from the device 101 described in reference to FIG. 2. In particular, the references 1 through 20, 108 through 110, 117 and 118 will not be described again. The device 102 makes it possible, in particular, to detect fluorescence and/or reflectance signals collected at the distal end of the guide, and makes it possible to quantify these signals and to construct, from these signals, images of the sample by fluorescence and by reflectance.

The device 103 also comprises a second illumination module 201 and a second detection module 204. The second illumination module 201 differs from the illumination module 1 in that it comprises only one source emitting an excitation beam, and does not comprise multiplexing means. The second detection module 204 differs from the detection module 4 in that it comprises only one detector, no filters and no demultiplexing means.

The second illumination 201 and detection 204 modules are optically conjugated with the scanning and injection optical system 6 in the same way as the illumination and detection modules of the second embodiment 102 illustrated in FIG. 3. In essence, the second illumination module 201 is optically conjugated with the scanning and injection module 2 by means of a second single-mode illuminating optical fiber 205 that is polarization maintaining, the second detection module 204 is optically conjugated with the scanning and injection module 2 by means of a second, multi-mode detecting optical fiber 207, and the scanning and injection module 2 comprises the polarizing cube 21 already described in reference to FIG. 3. The cube 21 is made to direct part of the excitation beam from the second illumination module 201 to the scanning and injection optical system 6 and to direct part of the collected luminous flux 14 to the second detection module 204.

The dichroic filter 20 and the polarizing cube 21 may be optically conjugated with the scanning and injection optical system 6 by the same beam splitter 22. The beam splitter 22 may be made to direct the excitation beams coming from the first or second illumination module to the scanning and injection optical system 6. The beam splitter 22 may be also made to direct the collected flux 14 partly to the first detection module 4 and partly to the second detection module 204. The part of the flux 14 directed to the first detection module 4 comprises the wavelength bands of the flux 14 directed by the filters 16a, 16b to the detectors 17, 18. The part of the flux 14 directed to the second detection module 204 comprises the wavelength or wavelength band of the excitation beam emitted by the second illumination module 201, so that the detector of the second detection module 204 is made to detect in the collected flux 14 a reflectance signal emitted by the sample in response to the excitation beam from the second illumination module 201. Thus, the second detection module 204 makes it possible to perform reflectance imaging of the sample. In essence, parasitic reflections of the excitation beam from the second illumination module 201 do occur, particularly in the scanning and injection optical system, but these parasitic reflections are rejected by the polarizing cube 21. The device 103 therefore makes it possible to simultaneously perform, using fibered confocal microscopy, reflectance imaging (and hence morphological imaging), by means of the second illumination module and the second detection module, and fluorescence imaging (and hence functional imaging), by means of the first illumination module and the first detection module, of the sample located in proximity to or in contact with the distal end of the guide 3.

In a first variant, the scanning and injection optical system 6, in the course of their various successive positions, may be made to alternately optically conjugate the first illuminating optical fiber 5, the first detecting optical fiber 7, the second illuminating optical fiber 205 and the second detecting optical fiber 207 with a single fiber of the image guide 3, so as to periodically scan all the fibers of the guide:

the first illuminating optical fiber 5, for a given position of the scanning and injection optical system (i.e. at a given instant), may be made to be optically conjugated with a first single fiber of the guide 3;

the first detecting optical fiber 7, for this same given position of the scanning and injection optical system, may be made to be optically conjugated with this first single fiber of the guide 3;

the second illuminating optical fiber 205, for this same given position of the scanning and injection optical system, may be made to be optically conjugated with this first single fiber of the guide 3; and the second detecting optical fiber 207, for this same given position of the scanning and injection optical system, may be made to be optically conjugated with this first single fiber of the guide 3.

This first variant makes it possible to simplify the construction of reflectance and fluorescence images.

In a second variant, the scanning and injection optical system 6, in the course of their various successive positions, may be made to alternately optically conjugate the first illuminating optical fiber 5 and the first detecting optical fiber 7 with a single fiber of the image guide, so as to periodically scan all the fibers of the guide, and to alternately optically conjugate the second illuminating optical fiber 205 and the second optical detecting fiber 207 with another single fiber of the image guide 3 so as to periodically scan all the fibers of the guide:

the first illuminating optical fiber 5, for a given position of the scanning and injection optical system (i.e. at a given instant), may be made to be optically conjugated with a first single fiber of the guide 3;

the first detecting optical fiber 7, for this same given position of the scanning and injection optical system, may be made to be optically conjugated with this first single fiber of the guide 3;

the second illuminating optical fiber 205, for this same given position of the scanning and injection optical system, may be made to be optically conjugated with a second single fiber of the guide 3, preferably adjacent to the first single fiber; and the second detecting optical fiber 207, for this same given position of the scanning and injection optical system, may be made to be optically conjugated with this second single fiber of the guide 3.

This second variant makes it possible to further reduce the parasitic reflections between the reflectance signals and the fluorescence signals, but requires a temporal registration of the reflectance and fluorescence images constructed.

Figure 5:
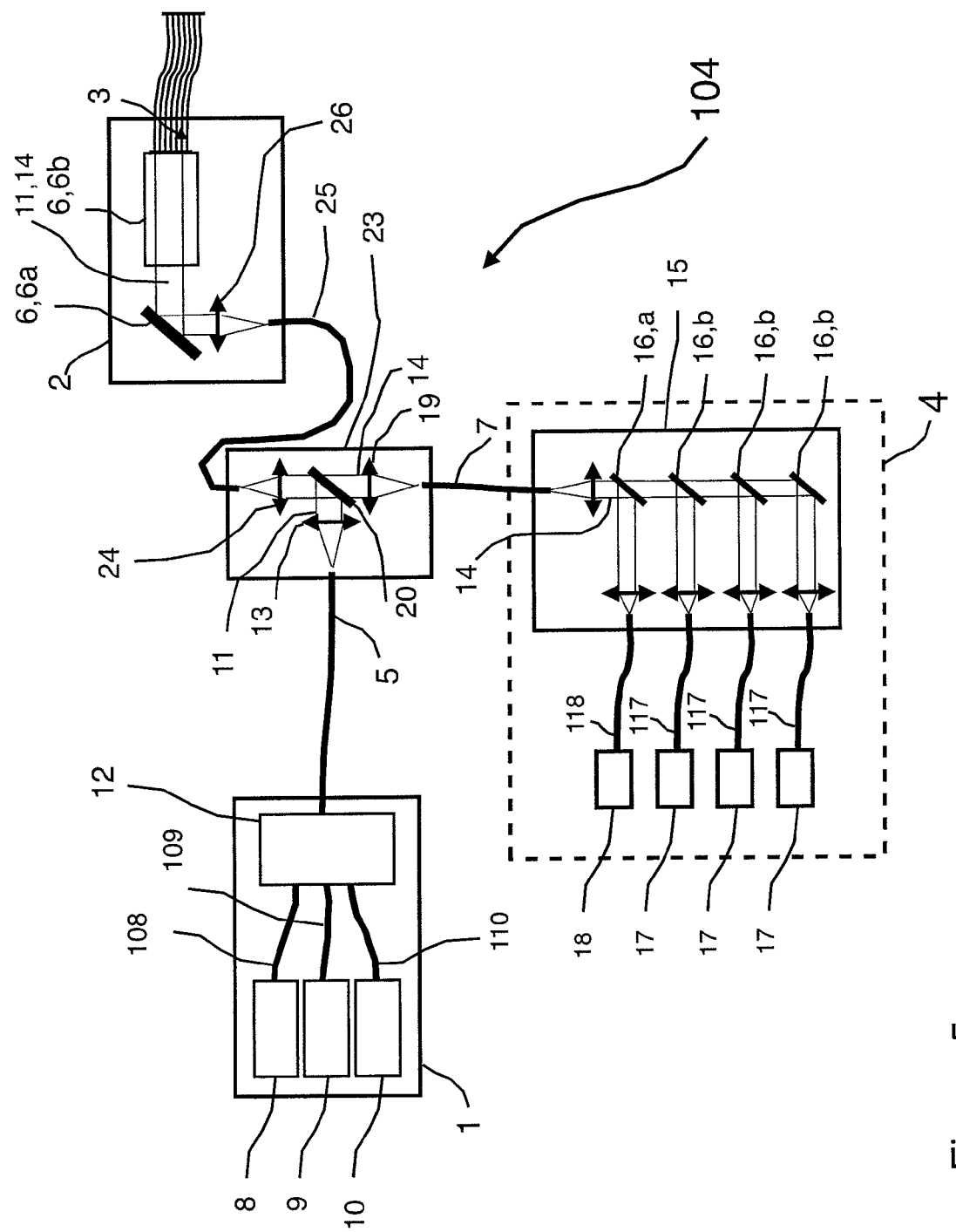
FIG. 5 is a view of a fourth embodiment of a device according to the invention.

We will now describe, in reference to FIG. 5, a fourth embodiment of the device 104 according to another embodiment of the invention, particularly applied to the fluorescence detection, quantification or imaging of the sample. The device 104 will only be described with respect to its differences from the device 101 described in reference to FIG. 2. In particular, the references 1 through 20, 108 through 110, 117 and 118 will not be described again.

Unlike in the first embodiment 101 described in reference to FIG. 2, the means 20 for splitting (i.e., beam splitter) the optical path of the excitation beams 11 from the optical path of the collected flux 14, and the optical systems 13 and 19, are disposed outside the scanning and injection module 2. Thus, the scanning and injection module may be completely independent of the wavelengths of the excitation beams 11 and the collected flux 14.

In essence, the device 104 comprises a splitting module 23. The splitting module 23 comprises a package inside which are grouped the optical systems 13, 19, another optical system 24, and the dichroic filter 20.

The illuminating fiber 5 can be disconnected from and reconnected to not only the package of the scanning and injection module, but also the package of the splitting module 23, by means of a connector or a similar device. Likewise, the detecting fiber 7 can be disconnected from and reconnected to not only the package of the scanning and injection module, but also the package of the splitting module 23, by means of a connector or a similar device. The splitting module 23 and the scanning and injection module 2 are optically conjugated by a two-core optical fiber 25.

The two-core fiber 25 comprises two substantially concentric fiber cores, the first core may be single-mode and made to transport the excitation beams 11, while the second core may be multi-mode and made to transport the collected luminous flux 14. One of the ends of the two-core fiber 25 can be disconnected from and reconnected to the package of the splitting module 23 by means of a connector, and the second end of the two-core fiber 25 can be disconnected from and reconnected to the package of the scanning and injection module 2 by means of a connector.

As in the first embodiment, the illuminating fiber 5 is made to guide the luminous excitation beams 11. The optical system 13 may be made to collimate the excitation beams guided by the illuminating fiber 5. The dichroic filter 20 may be made to direct the collimated excitation beams 11 to the scanning and injection optical system 6, and to direct the collected flux 14 to the detection module 4.

Unlike in the first embodiment, the dichroic filter 20 may be made to direct the excitation beams 11 to the optical system 24 and the two-core fiber 25. The optical system 24 is made to focus the excitation beams 11 into the input of the two-core fiber 25 toward the scanning and injection module 2. The two-core fiber 25 may be made to guide the excitation beams 11 along its first core to the scanning and injection module 2. In addition, the two-core fiber may be made to guide the collected flux 14 along its second core to the splitting module 23. The optical system 24 may be made to collimate the collected flux 14, and the dichroic filter 20 may be made to direct the collected and collimated flux 14 to the detecting fiber 7. The optical system 19 may be made to focus the collected flux 14 reflected by the filter 20 into the input of the detecting fiber 7 toward the detection module 4.

The scanning and injection module 2 may also comprise an optical system 26 made to collimate the excitation beams 11 coming from the splitting module 23 and directed to the scanning and injection optical system 6, and to focus the collected flux 14 into the input of the two-core fiber 25 toward the splitting module 23.

In the device 104, the illumination module 1 may be optically conjugated with the scanning and injection module 2 by means of the illuminating optical fiber 5 and the two-core fiber 25. Likewise, the detection module 4 may be optically conjugated with the scanning and injection module 2 by means of the detecting optical fiber 7 and the two-core fiber 25.

If the first core of the two-core fiber 25 is a single-mode Gaussian fiber, it gives the excitation beam a high single-mode Gaussian quality and provides an optimal rate of injection of the excitation beams 11 into the image guide 3. Thus the two-core has the function of performing a mode filtering of the excitation beams. In addition, if the second core is multi-mode, the two-core fiber has the function of not performing a mode filtering on the collected flux 14, for the same reasons as the detecting fiber 7.

Finally the two-core fiber 25, for a given position of the scanning and injection optical system, may be made to be optically conjugated with a single fiber of the guide 3. In essence, for a given position of the scanning and injection optical system 6, the excitation beams 11 transported by the two-core fiber 25 are only injected into one fiber of the guide, and the diameter and position of the second core are calculated so that the second core transports a collected luminous flux 14 that has only been guided along this one fiber of the guide. Thus, the two-core fiber 25 may have the function of performing a spatial filtering of the collected flux 14, and give the device 104 its confocality.

The technical characteristics of the dichroic filter 20 are dependent on the wavelengths of the excitation beams 11 and of the collected flux 14. A change in the wavelength of any of the excitation beams may require replacing the multiband filter 20. This change can be made easily by replacing the splitting module 23 with a new splitting module comprising a new dichroic filter 20, without having to optically realign the device 104 or any of the modules of the device 104.

Figure 6:
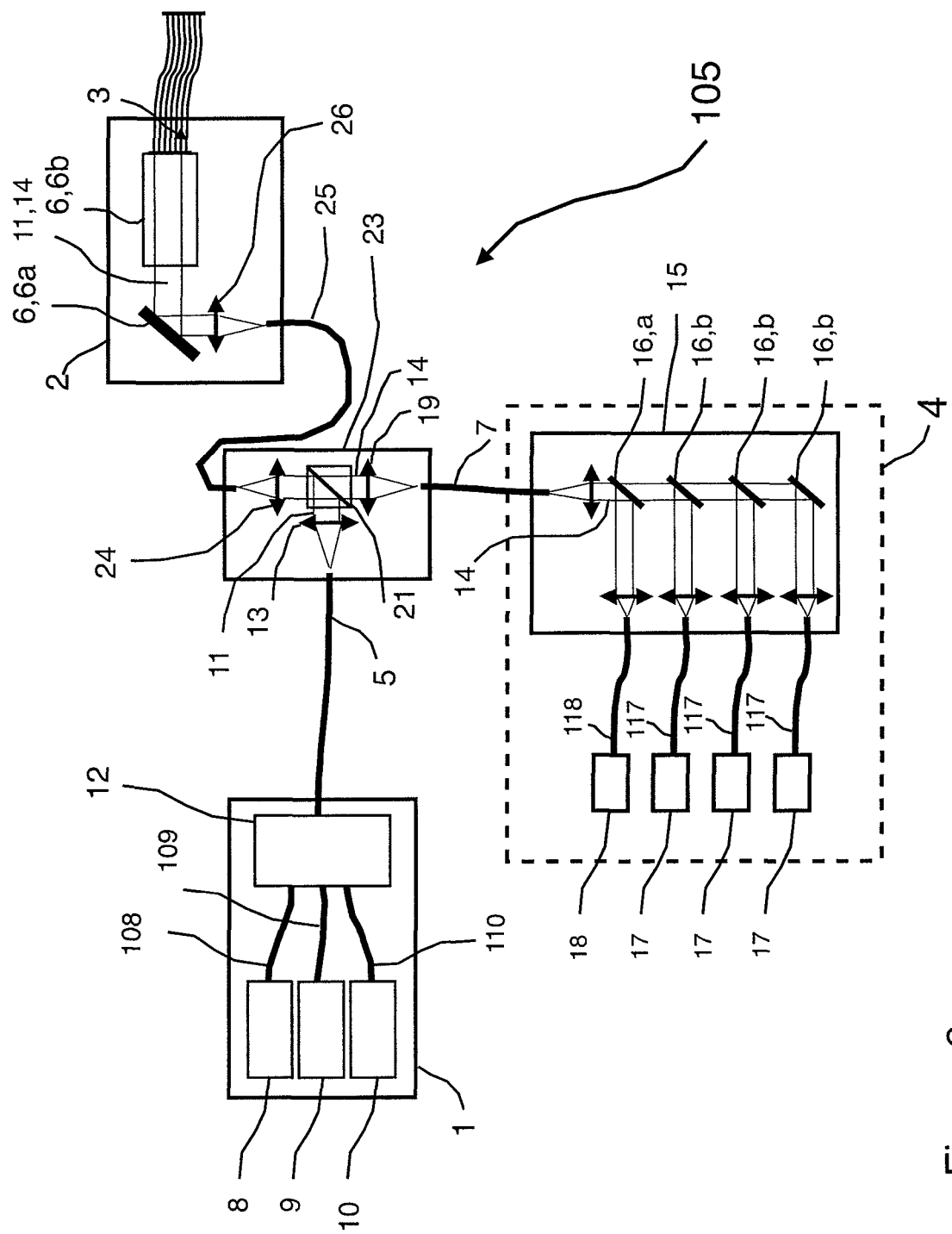
FIG. 6 is a view of a fifth embodiment of a device according to the invention.

Lastly, we will describe, in reference to FIG. 6, a fifth embodiment of a device 105 according to another embodiment of the invention. The device 105 will only be described with respect to its differences from the device 104 described in reference to FIG. 5. In particular, the references 1 through 19, 21, 23 through 26, 108 through 110, 117 and 118 will not be described again. The device 105 may make it possible, in particular, to detect fluorescence or reflectance signals collected at the distal end of the guide, and makes it possible to construct images of the sample by fluorescence or by reflectance.

In the device 105, the dichroic filter 20 of the splitting module 23 has been replaced by the polarizing cube 21 described in reference to FIG. 3. As in the second embodiment of the device according to the invention, the polarizing cube 21 may make it possible to use one of the detectors 18 and one of the laser sources 8 for reflectance imaging. In essence, the polarizing cube 21, as described in reference to FIGS. 3 and 4, rejects the parasitic reflections of the excitation beam from the laser source 8 used for reflectance. In order not to lose intensity in the excitation beams 11 directed to the scanning and injection optical system, all of the fibers guiding the excitation beams 11 to the scanning and injection optical system 6 (i.e., the source fibers 108 through 110, the illuminating fiber 5 and the first core of the two-core fiber 25) may be polarization maintaining fibers, resulting in an increased production cost.

The exemplary dimensions of the elements in the various embodiments described above may be as follows:
core diameter of the detecting fiber 7: 50 micrometers
core diameter of the demultiplexing fibers 117, 118: 62.5 micrometers
core diameter of the illuminating fiber 5: 4 micrometers
diameter of the single-mode core of the two-core fiber 25: 4 micrometers, and
diameter of the multi-mode core of the two-core fiber 25: 10 micrometers.

The above described dimensions and various configurations of embodiments of the invention are for illustration only.

One skilled in the art would understand that the invention is not limited to the examples described above, and many modifications can be made to these examples without departing from the scope of the invention.

In particular, a source of an excitation beam may be a multi-wavelength laser, i.e. a laser that simultaneously emits several wavelengths or wavelength bands.

Likewise, a source of an excitation beam may be an adjustable wavelength laser, a Light-Emitting Diode (LED), a wide-spectrum lamp or a supercontinuum.

In addition, the multiplexing means may be, for example, phase- or fiber-multiplexing means, and may comprise, for example, a junction that fuses the cores of the demultiplexing fibers 117, 118 in the core of the detecting fiber 7. The description is nonlimiting in terms of the number of sources per illumination module and the number of detectors per detection module.

The device according to the invention can comprise several multiplexers in series and/or in parallel between the excitation sources and the scanning and injection module.

According to embodiments of the invention, the fibers of the image guide may be all multi-mode or all single-mode fibers, or can comprise a mixture of multi-mode and single-mode fibers.

Furthermore, at least one of the dichroic filters of a detection module or the dichroic filter of a splitting module may be a dynamic dichroic filter wherein the wavelength bands it reflects or transmits can be dynamically controlled. Such a dynamic dichroic filter can for example comprise an acousto-optical modulator or an electro-optical modulator wherein a command applied to the modulator makes it possible to control the wavelength bands.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

The invention claimed is:

1. An imaging device, comprising:
an illumination module comprising at least one emitter for emitting at least one excitation beam;
a scanning and injection module comprising an image guide, a proximal end and a distal end of which are linked by a plurality of optical fibers, and a scanning and injection optical system configured to alternately inject the at least one excitation beam into an optical fiber of the image guide from the proximal end of the image guide;
a detection module comprising at least one detector for detecting at least one luminous flux collected at the distal end of the image guide,
wherein at least one of the illumination module and the detection module is optically conjugated with the scanning and injection module by a conjugating optical fiber.

2. The imaging device according to claim 1, wherein the conjugating optical fiber, for a given position of the scanning and injection means, is optically conjugated with a single fiber of the image guide.

3. The imaging device according to claim 1, further comprising a connector for disconnecting and reconnecting the conjugation via the conjugating optical fiber.

4. The imaging device according to claim 1, wherein the illumination module is optically conjugated with the scanning and injection module by an illuminating optical fiber.

5. The imaging device according to claim 4, wherein the illuminating optical fiber is made to perform a mode filtering of the at least one excitation beam.

6. The imaging device according to claim 5, wherein the illuminating optical fiber is a single mode fiber.

7. The imaging device according to claim 4, wherein the at least one emitter comprises a plurality of emitters each comprising a source for emitting an excitation beam, and wherein the illumination module further comprises a multiplexing device for multiplexing the excitation beams in a single optical fiber.

8. The imaging device according to claim 7, wherein each source is optically conjugated with the multiplexing device by a source optical fiber, and wherein the multiplexing device comprises a fiber multiplexer that fuses the cores of the source optical fibers.

9. The imaging device according to claim 1, wherein the detection module is optically conjugated with the scanning and injection module by a detecting optical fiber.

10. The imaging device according to claim 9, wherein the scanning and injection optical system is configured to guide the collected luminous flux to the detection module.

11. The imaging device according to claim 10, wherein the detecting optical fiber is configured to perform a spatial filtering of the collected luminous flux and, for a given position of the scanning and injection optical system, is optically conjugated with the fiber of the image guide into which the scanning and injection optical system is configured to inject the at least one excitation beam, and is configured to reject light coming from other fibers of the image guide.

12. The imaging device according to claim 9, wherein the detecting optical fiber is a multi-mode optical fiber.

13. The imaging device according to claim 9, wherein the detection module comprises a demultiplexer for wavelength demultiplexing the collected luminous flux.

14. The imaging device according to claim 13, wherein the detection module comprises several detectors, each detector being configured to detect a given wavelength band of the demultiplexed luminous flux.

15. The imaging device according to claim 1, wherein the scanning and injection optical system is configured to guide the luminous flux collected at the distal end of the image guide to the detection module, and wherein the scanning and injection optical system comprises a beam splitter to direct the at least one excitation beam to the scanning and injection optical system and to direct the collected luminous flux coming from the scanning and injection optical system to the detection module.

16. The imaging device according to claim 15, wherein the beam splitter comprises a dichroic filter.

17. The imaging device according to claim 15, wherein the beam splitter comprises a beam-splitting cube, and wherein the illumination module and the detection module are configured for reflectance imaging.

18. The imaging device according to claim 1, wherein the beam splitter is part of a splitting module, and wherein the detection module and the illumination module are optically conjugated with the scanning and injection module by the splitting module and a splitting optical fiber that conjugates the splitting module with the scanning and injection module.

19. The imaging device according to claim 18, wherein the splitting optical fiber comprises two substantially concentric fiber cores, the first core being single-mode and configured to transport the at least one excitation beam, the second core being multi-mode and configured to transport the collected luminous flux.

20. A scanning and injection module, comprising:
an image guide comprising a proximal end and a distal end linked by a plurality of optical fibers;
a conjugation optical system configured for optically conjugating the scanning and injection module with an illumination module that comprises at least one emitter for emitting at least one excitation beam, and with a detection module that comprises at least one detector for detecting a luminous flux collected at the distal end of the image guide; and
a scanning and injection optical system configured to alternately inject the at least one excitation beam into an optical fiber of the image guide from the proximal end of the image guide,
wherein the conjugation optical system is so configured that at least one of the illumination module and the detection module is optically conjugated with the scanning and injection module by a conjugating optical fiber.

21. The scanning and injection module according to claim 20, wherein the conjugation optical system is so configured that the conjugating optical fiber, for a given position of the scanning and injection module, is optically conjugated with a single optical fiber of the image guide (3).

22. The scanning and injection module according to claim 20, wherein the conjugation optical system comprises the conjugating optical fiber, which is integral with the module.

23. The scanning and injection module according to claim 20, wherein the conjugation optical system comprises a connector for disconnecting the conjugating fiber from and reconnecting it to the scanning and injection module.

24. The scanning and injection module according to claim 20, wherein the conjugation optical system comprises means for optically conjugating the scanning and injection module with the illumination module via an illuminating optical fiber, and in that these conjugation means are made so that the illuminating fiber, for a given position of the scanning and injection means, is optically conjugated with the fiber of the guide into which the scanning and injection means are made to inject the at least one excitation beam.

25. The scanning and injection module according to claim 20, wherein the conjugation optical system comprises means for optically conjugating the scanning and injection module with the detection module via a detecting optical fiber, wherein the scanning and injection optical system is configured to guide the collected luminous flux to the detection module, and wherein the conjugation optical system is so configured that the detecting optical fiber, for a given position of the scanning and injection module, is optically conjugated with the optical fiber of the image guide into which the scanning and injection optical system is configured to inject the at least one excitation beam.

26. An imaging method, comprising:
emitting at least one excitation beam from an illumination module,
alternately injecting, using a scanning and injection module, the at least one excitation beam into an optical fiber of an image guide, which comprises a proximal end and a distal end linked by a plurality of optical fibers, from a proximal end of the image guide,
detecting, using a detection module, a luminous flux collected at a distal end of the image guide, and
optically conjugating, using a conjugating optical fiber, at least one of the illumination module and/or the detection module with the scanning and injection module.

27. The method according to claim 26, wherein the optically conjugating with the scanning and injection module comprises an optical conjugation of the conjugating optical fiber with a single optical fiber of the image guide.

28. The method according to claim 26, wherein the optically conjugating with the scanning and injection module comprises guiding the at least one excitation beam from the illumination module to the scanning and injection module along an illuminating optical fiber.

29. The method according to claim 28, further comprising modal filtering the at least one excitation beam using the illuminating optical fiber.

30. The method according to claim 28, spatially superpositioning several excitation beams in the illuminating optical fiber.

31. The method according to claim 26, wherein the optically conjugating the scanning and injection module comprises guiding the collected luminous flux from the scanning and injection module to the detection module along a detecting optical fiber.

32. The method according to claim 31, a further comprising spatially filtering, using the detecting optical fiber, the collected luminous flux, so that the detecting optical fiber is alternately optically conjugated with the optical fiber of the image guide, into which the at least one excitation beam is alternately injected.

* * * * *